United States Patent [19]
Lin et al.

[11] Patent Number: 5,849,891
[45] Date of Patent: Dec. 15, 1998

[54] SATELLITE RNA FROM BAMBOO MOSAIC VIRUS AS A VECTOR FOR FOREIGN GENE EXPRESSION IN PLANTS

[75] Inventors: Na-Sheng Lin; Yau-Heiu Hsu, both of Taipei, Taiwan

[73] Assignee: National Science Council, Taipei, Taiwan

[21] Appl. No.: 511,717

[22] Filed: Jul. 28, 1995

[51] Int. Cl.⁶ .......................... C12N 15/11; C12N 15/63; C12N 15/66; C12Q 1/70
[52] U.S. Cl. ..................... 536/23.1; 435/320.1; 435/5
[58] Field of Search ................ 536/23.1; 435/320.1, 435/5

[56] References Cited

PUBLICATIONS

Masuta, et al., GenBank accession No. M17182, 1987.

Primary Examiner—Nancy Degen
Assistant Examiner—Matthew Latimer
Attorney, Agent, or Firm—Jeing & Chang

[57] ABSTRACT

A satellite RNA was found to be naturally associated with bamboo mosaic virus (BaMV-V) isolated from infected *Bambusa vulgaris* McClure. Nucleotide sequence revealed that this satellite RNA genome contains 836 nucleotides and encodes a 20 kDa protein. Infectious transcripts have been generated from full length cDNA downstream T7 RNA polymerase promoter. Precise replacement of open reading frame (ORF) of cDNA of satellite RNA with sequence encoding bacterial CAT (chloramphenicol acetyltransferase) resulted in high level expression of CAT in infected dicotyledon plants, *Chenopodium quinoa* and tobacco (*Nicotiana benthamiana*) in the presence of baMV genomic RNA. Thus, this satellite system is potentially useful as a satellite-based plant expression vector.

36 Claims, 8 Drawing Sheets

```
  1 gaaaactcaccgcaacgaaACGAAACAAATCGTTCAGAAACACTAGACCAC        51
 52 GAGGGCCCCCTATAGTCCCGCTGAGGGTGTGGCAGGCCCCGTGCGATAGG        102
103 CTAACTGTGGTGTTCCCCGCACTCCGTCGAGCGGTTAATACGACGCTTACC       153
154 AAGACGATGGTTCGGAGGAGAAATCGTCGCCAGAGATCGCGTGTCTCCCAA       204
       M  V  R  R  N  R  R  Q  R  S  R  V  S  Q
205 ATGACCGACATCATGTATGGCTCACTAACACTGGGCAGTACCACAACATGG       255
     M  T  D  I  M  Y  G  S  L  T  L  G  S  T  T  T  W
256 ACCAGGAAGAATTTCCCTGGGTTGGCCAATATGGGAGATCGACCTTTCCAG       306
     T  R  K  N  F  P  G  L  A  N  M  G  D  R  P  F  Q
307 GTCATCTCTGTTAAAATTGTGTCTCGTCTGCCTCCCCCATGCTTTACCAA        357
     V  I  S  V  K  I  V  V  S  S  A  S  P  M  L  Y  Q
358 GCCAGGCTTTACTCACCACACGATGATGACAATGTGGGTCACCGGGCTT         408
     A  R  L  Y  S  P  H  D  D  D  N  V  G  S  T  G  L
409 CAAATGTCTGGAACCACTCCACACACTCACCATATGAGAGCTCTGCCAGGT       459
     Q  M  S  G  T  T  P  H  T  H  H  M  R  A  L  P  G
460 CAAAACACCTGTTTAGTGGCAACACGAGCTCTACTCAGGTGATTGTCGCC        510
     Q  N  T  W  F  S  G  N  T  S  S  T  Q  V  I  V  A
511 ATTGATGGCCTGAAGACGAAGACAACGGATGCCACGCCCCAGAACGCGGTG       561
     I  D  G  L  K  T  K  T  T  D  A  T  P  Q  N  A  V
562 GCCGTTCAGGTGTTCTATCGAGTGGCGCCGAGCGAACTCCAGAGCGCAACT       612
     A  V  Q  V  F  Y  R  V  A  P  S  E  L  Q  S  A  T
613 GGTAATGCTGAAATGCCTACAACCACGCCTTTTGACCTCCCAGAGGGGTAT       663
     G  N  A  E  M  P  T  T  T  P  F  D  L  P  E  G  Y
664 GAATACCTCGCTGACGCGTGGCTCCCTGACCGTGCACCAACCAGTTGATCC       714
     E  Y  L  A  D  A  W  L  P  D  R  A  P  T  S  *
715 ACGAGCACAACCGGCTTGTCAATGAGCCGCCAGGTTTAGCCTGGTTCCACA       765
766 TTGACCCACCACCCATACTATGAGACCTAACCAGTAGTGGTGGTCGTCCCG       816
817 AATAAAGACGCTAAAGATGA
```

Fig. 3

SATELLITE RNA FROM BAMBOO MOSAIC VIRUS AS A VECTOR FOR FOREIGN GENE EXPRESSION IN PLANTS

BACKGROUND OF THE INVENTION

Transgenic plants have been widely used for the expression of foreign genes in plants. Conventionally, this can be accomplished by transforming the target plants through a variety of means such as *Agrobacterium tumefaciens* infection, particle gun bombardment, or electroporation. The plants so transformed, however, have to depend upon plant tissue culture techniques for regeneration. To achieve stable transformation from tissue cultures is not only time and labor consuming but also requires the screening of numbers of transformats under the control of suitable promoters. Therefore, it has become a better choice to use modified plant viral vectors for foreign gene expression by taking advantages of the vectors' abilities for self-replication and systemic infection in plants. Moreover, the infection may frequently yield a high level of virus accumulation in the infected plants within 1–2 weeks, rather than the months or longer required for the plant regeneration.

Although the viral vectors provide many advantages over the conventional plant tissue culture related techniques, the viral vectors nevertheless have their own limitations. For instances, the replication of viral vectors is often affected by the modifications of viral genome for the purposes of vector constructions or foreign gene insertion. In addition, foreign genes are often lost due to the recombination of the viral genome after few generations of replication.

Many attempts have been made to overcome this problem. Recently, a successful example is the development of tobacco mosaic virus (TMV) as a vector to express biologically active α-trichosanthin (*Proc. Natl. Acad. Sci. USA* 90: 427–430, 1993) and the antihypertension polypeptides (i.e., angiotensin-I-converting enzyme inhibitor) (*Biotechnology* 11: 930–932, 1993) in tobacco and tomato, respectively. As to the development of plant viral satellite RNA as a vector, only one example is reported in a Japanese patent (JP. No. 2053491, 1990) in which a satellite RNA from cucumber mosaic virus (CMV) was used as a vector, and a cDNA fragment of 120 bps was inserted covering the 3' end untranslated region of potato virus Y (PVY). The resulted chimeric transcripts reduced the symptom on the infected crops caused by the CMV in three weeks. However, since satellite RNA associated with CMV is only 369 nucleotides long, its capacity for the insertion of a foreign gene is relatively limited.

In general, satellite RNAs are short RNA molecules with an average of 200–1500 nucleotide in length. They share no significant sequence homology to the viral genomic RNA and are dependent on helper viruses for their replication, encapsidation and movement (*Microbiol. Rev.* 56: 256–279, 1992). Satellite RNAs can be broadly classified into two groups on the basis of their coding capacity. The smaller satellites with approximately 300 nucleotides in length do not contain any functional open reading frames (ORFs) but their structures are highly specialized, e.g. satellite RNA associated with CMV. Therefore, the small satellite RNAs are not preferred vectors because their capacities for foreign gene fragments insertion are quite limited. On the other hand, the larger satellite RNAs contain functional ORF and are mostly associated with nepoviruses. In most cases, the proteins encoded by the larger satellites are required for their replication (*Biochimie* 75: 561–567, 1993). Thus, the ORFS are indispensable and can not be replaced with a foreign gene without losing their replication abilities. It becomes apparent that there is a need for a larger satellite RNA suitable as a vector whose ORF is dispensable for their replication and can be replaced with a foreign gene.

Bamboo mosaic virus (BaMV) has properties suggesting that it belongs to the potexvirus group (*Phytopathology* 82: 731–734, 1992; *J. Gen. Virol.* 75: 2513–2518, 1994). The genome of BaMV consists of a 6.4 Kb single-stranded, positive-sense RNA. Recently, we obtained a BaMV isolated (designated BaMV-V) from infected common bamboo (*Bambusa vulgaris* MuClure). By comparison with the previously described isolate (designated BaMV-O) (*Phytopathology* 81: 1551–1555, 1991; *Phythpathology* 82: 731–734, 1992), we found that the BaMV-V isolate contained an additional RNA molecule (sBaMV). On the basis of Northern hybridization, nucleotide sequence analysis, infectivity assay, and other tests, we concluded that it is a naturally occurring satellite RNA associated with BaMV-V. This satellite RNA is the first one found to be associated with potexvirus. Moreover, the ORF of sBaMV is dispensable for their replication and can be replaced with a bacterial gene, chloramphenicol acetyltransferase (CAT). The inserted CAT gene was rapidly and abundantly expressed in the infected plants co-inoculated with the BaMV genomic RNA.

It is therefore an object of the present invention to isolate, identify and determine the complete nucleotide sequence of a novel satellite RNA associated with BaMV.

It is a further object of the present invention to synthesize biologically active cDNA clones of sBaMV and to produce infectious in vitro transcripts of said clones in the presence of the BaMV genomic RNA.

It is yet another object of the present invention to provide a satellite-based vector whose ORF can be replaced by a foreign gene and infection of the chimeric transcripts together with BaMV genomic RNA will result in the rapid expression of the foreign genes in plants.

SUMMARY OF THE INVENTION

The present invention relates to the isolation of a satellite RNA from infected bamboos, the nucleotide sequence analysis of this satellite RNA, and the development of this satellite RNA as a satellite-based vector for the expression of a foreign gene in the infected plant.

One aspect of the present invention relates to the isolation, purification and characterization of a satellite RNA from BaMV. The BaMV-infected leaves of common bamboo (*Bambusa vulgaris* McClure) showing mosaic symptom of the present invention were collected from the Taipei Botanical Garden. After virus purification, RNA extraction and gel electrophoresis, it was found that BaMV-V contained not only the genomic RNA (designated L-RNA) with the size of about 6400 nucleotides, but also a RNA molecule (designated sBaMV) with the size of about 850 nucleotide.

To characterize the nature of sBaMV, Northern blot hybridization was performed to analyze the relationship between BaMV genomic RNA and sBaMV. The virus genomic RNA-specific probe (L-cDNA probe) hybridized to the L RNAs of BaMV-o and BaMV-V, but not to the sBaMV. By contrast, the sBaMV-specific probe (S-cDNA) hybridized to sBaMV RNA only, but not to gemonic RNAs of BaMV. The lack of cross-hybridization between RNAs and the heterologous probes indicates that there is no sequence homology between genomic RNA and sBaMV.

In order to test the replication dependency, sBaMV RNA was purified from 1% non-denaturing agarose gel for inoculation. It was confirmed that sBaMV alone cannot infect either Chenopodium quinoa or barley protoplasts. Furthermore, in vitro rabbit reticulocyte lysate (RRL) translation studies, it was found that the sBaMV coded for a 25 kDa polypeptide which was not immunoprecipitated with antiserum against BaMV capsid protein.

Based on the results of Northern hybridization, inoculation experiment and in vitro translation products analysis, it was confirmed that sBaMV is a satellite RNA naturally associated with BaMV.

Another aspect of the invention is to provide for a novel RNA molecule from sBaMV on the basis of the cDNA nucleotide sequence analysis. Using gel-eluted sBaMV RNA as a template, double-stranded cDNA was synthesized according to the Riboclone cDNA synthesis system (Promega), cloned into pUC119 plasmid for nucleotide sequence analysis. As shown in FIG. 3, the sBaMV contains a total of 836 nucleotide, excluding the poly (A) tail, with the base composition of 25.5% A, 29.3% C, 24.8% G, and 20.4% U. Compared to the nucleotide sequences in the GenBank, sBaMV has no sequence homology with any known genes, viruses, or satellite RNAs. It is indeed a new satellite RNA and sequence data has been deposited to the EMBL/GenBank Data Libraries under Accession No. L22762.

One more aspect of the invention is to provide for infectious in vitro transcripts of sBaMV. Using purified sBaMV RNA as a template, cDNA to the sBaMV was synthesized with primer (5'-GTCGACTCTAGA(T)$_{15}$-3'). The oligonucleotides containing T7 polymerase promoter was used to synthesize the second strand cDNA. The full-length double-stranded cDNA was isolated and cloned into pUC119. The resulting plasmid pBSF4 contained the full length cDNA of sBaMV (FIG. 8).

The in vitro transcripts BSF4 were synthesized from xbaI-linearized pBSF4 in an in vitro transcription reaction. Northern blot analysis detected the 6.4 kb genomic RNA and sBaMV-specific sequences in barley protoplasts or C. quinoa coinoculated with Ba MV-L RNA and BSF4, indicating that the BSF4 is infectious in the presence of BaMV-L RNA.

Still another aspect of the present invention is to provide for an isolate of sBaMV whose ORF is dispensable for its replication. To determine whether the ORF is essential in sBaMV replication, a series of frameshift and deletion mutations were introduced into the ORF of pBSF4 (FIG. 6). For instance, pBSFS, the start codon 160-AUG was changed into 160-UUG; pBSF6, a nucleotide C was inserted after the start condon 160-AUG which led to a frameshifting; pBSF7, 38 nucleotide were deleted from nucleotide 449–488; pBSFB, 282 nucleotide were deleted from nucleotide 279–560, pBSF9, sequences encoding the ORF of 20 kDa were completely removed.

Northern blot analysis of total RNAs extracted from infected barley protoplasts or C. Quinoa revealed that all the mutants were able to replicate in cells in the presence of BaMV-L RNA. Deletion of the entire ORF in BSF9, however, substantially reduced the replication activity to about 0.5–1.0% of BSF4. Thus, the sBaMV-encoded protein is not essential for sBaMV replication and is dispensable.

Another unique aspect of the present invention is to provide for a sBaMV-based vector which is capable of expressing a foreign gene in plants. Since the sBaMV-encoded protein is not required for its replication, the chimeric plasmid pBSCAT was constructed by substituting the reporter gene CAT (Chloramphenicol acetyltransferase) coding sequence for the ORF of pBSF4. The hybrid transcripts were replicated well in protoplasts and C. quinoa coinfected with BaMV-L RNA. Considerable CAT activity was detected by CAT-ELISA assay (Boehringer Mannheim GmbH) in extracts of infected C. quinoa leaves. In assays using commercial CAT enzyme (BM) as a standard, 2.0 μg of CAT enzyme was produced per gram of C. quinoa leaves. Thus, sBaMV is potentially useful as a satellite-based vector.

One more feature of the present invention is to provide a sBaMV-based vector which can amplify and accumulate foreign gene products to a high concentration in the infected plants within 1–2 weeks. This system is time and labor saving being much faster rather than the months or longer time period required for the regeneration of transgenic plants.

In addition, the host range of BaMV and sBaMV includes monocot plants, e.g. host plant bamboos, barley and corn as well as dicot plants, e.g. C. quinoa and Nicotiana benthamiana etc. In the presence of BaMV genomic RNA, foreign genes can be amplified in those plants without affecting agronomy traits.

Furthermore, the satellite RNA-based vector has several advantages over other previously reported plant RNA viral vectors. First, satellite vector usually replicate in higher copy numbers than the viral genomic RNA. Second, in the construct pBSCAT the ORF was replaced by the CAT gene, whereas in other viral vectors the foreign gene was inserted as an addition to the viral genome. Thus, in the present invention the factors associated with gene instability resulting from homologous and nonhomologous recombination can be greatly reduced. Additionally, the sBaMV belongs to large satellite RNAs and thus, has more capacity for the insertion of foreign genes with larger molecular weight compared to the small satellite RNAs.

Still one more aspect of the present invention is to provide for a plant expression system for the production of biologically active or pharmaceutically important polypeptides. In addition to bacterial reporter gene CAT, the sBaMV vector in this invention can also successfully express the 3A movement protein of CMV in the infected cells in our laboratories. Thus, any potential or interested genes can be expressed in the plants through this vector. For example, the ribozyme containing the sequence specific to BaMV capsid protein can be developed to reduce disease caused by BaMV; the surface antigen of Heptatis B virus can be produced in plants as clinical vaccine; and all other pharmaceutical enzymes, polypetides, or proteins can be potentially expressed to change amino acid contents in plants.

BRIEF DESCRIPTION OF THE FIGURES

FIG. 3. The complete nucleotide sequence of sBaMV RNA (SEQ ID NO: 1) and the deduced amino acid sequence of the encoded protein (SEQ ID NO: 2).

DETAILED DESCRIPTION OF THE INVENTION

The objects, specifications and advantages of the present invention are further illustrated by the following examples and figures. The examples are for explanation purposes and not limited to the present invention.

EXAMPLE 1

Satellite RNA Isolation, Extraction and Northern Blot Analysis

Figure 1:
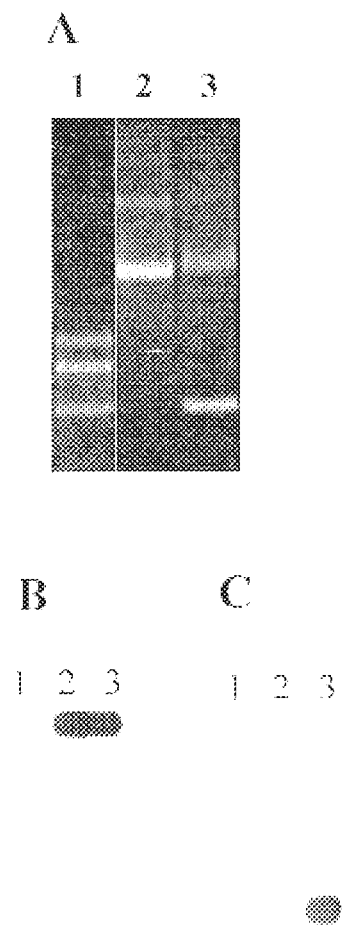
FIG. 1. Gel electrophoresis (A) and Northern blot hybridization (B,C) of viral RNAs. (A) RNAs extracted from purified CMV (Lane 1), BaMV-O (Lane 2) and BaMV-V (Lane 3) were separated by electrophoresis in a 1% agarose gel in Tris-borate buffer and stained with ethidium bromide; (B,C) RNA samples resolved in the gel as FIG. 1A. were transferred to H-Bond hybridization membrane. The RNAs were hybridized with $^{32}$p-labeled cDNA transcribed from (B) randomly primed BaMV L RNA (L-cDNA probe) and with (C) oligo (dT)$_{15}$ primed sBaMV RNA (S-cDNA probe).

Bamboo mosaic virus (designated BaMV-V) was purified from infected common bamboo (*B. vulgaris* McClure) (*Plant Dis.* 77: 448–450, 1993), collected from Taipei Botanical Garden, showing mosaic symptoms, by the methods of Lin et. al. (*Phytopathology* 81:1551–55, 1991). RNA was further extracted and separated in 1% agarose gel with TBE buffer (pH 8.0) by electrophoresis (*Phytopathology* 82: 731–734, 1992). The isolate of BaMV-O (*Phytopathology* 81: 1551–1555, 1991; 82: 731–734, 1992) was used as a control. As shown in FIG. 1(A), BaMV-O virions contain a genomic RNA with only 6400 nucleotide only (designated L RNA) (lane 2), but the BaMV-V virions contain an additional RNA species of about 850 nucleotide (designated sBaMV) (lane 3), which is larger than the satellite RNA associated with CMV (lane 1, lowest band).

In order to determine the relationship between BaMV L RNA and sBaMV, Northern blot hybridization was performed. FIG. 1B shows that the BaMV genomic RNA-specific probe (designated L-cDNA probe) hybridized to the L RNAS of BaMV-O (lane 2) and BaMV-V (lane 3), but not to the satellite RNA of CMV (lane 1) or sBaMV (lane 3). By contrast, the sBaMV-specific probe (designated S-cDNA probe) hybridized to the sBaMV only (FIG. 1C, lane 3), but not to the other RNA species. The lack of cross-hybridization between RNAs and the heterologous probes indicates that there is no sequence homology between BaMV-L RNA and sBaMV.

EXAMPLE 2 sBaMV Isolation and Inoculation

BaMV-V RNA was separated by electrophoresis in 1% nondenatured low-melting point agarose gel (Bethesda Research Laboratories, Gaithersburg, Md.). After electrophoresis, the two RNAs of BaMV-V, the genomic RNA (L RNA) and sBaMV RNA, were isolated from slices of gel by phenol extraction and ethanol precipitation. The purified RNAs were dissolved in sterile distilled water, quantitated by UV absorption, and stored at −70° C. until use.

To obtain the BaMV-V isolate free of sBaMV, the gel-purified L RNA of BaMV-V was inoculated onto *C. quinoa*. The inoculum consisted of 1 μg RNA in 100 μl inoculation buffer (0.05M K$_2$HPO$_4$, 0.1M glycine, 100 μg/ml bentonite, pH 9.3). Local lesions were shown 7–10 days post-infection. After three successive local lesion transfers, the isolate was propagated in *C. quinoa* and designated as BaMV-L. Prior to inoculation, BaMV-L and sBaMV RNA were shown to be free of contamination from of each other by hybridization.
a. Plant Inoculation When the sBaMV RNA (1 μg/100 μl inoculation buffer) alone was mechanically inoculated onto *C. quinoa*, no local lesions were produced and no sBaMV RNAs were detected when dot blot hybridization with S-cDNA probe was performed with total RNAs extracted from the inoculated leaves. However, L RNA samples of purified BaMV-O or BaMV-L at the same concentration produced an average of about 180 local lesions on the inoculated leaves. Thus sBaMV alone can not replicate in the *C. quinoa*.
b. Protoplast Inoculation Young leaves from seven-day-old barley seedlings were the major sources for the isolation of mesophyll protoplasts. The procedures for protoplast isolation, viral RNA inoculation, protoplast total RNA extraction and Northern hybridization were carried out as described by the inventor (*Bot. Bull. Acad. Sin.* 33: 271–275, 1992; *Phytopathology* 82: 731–734, 1992).

Figure 2:
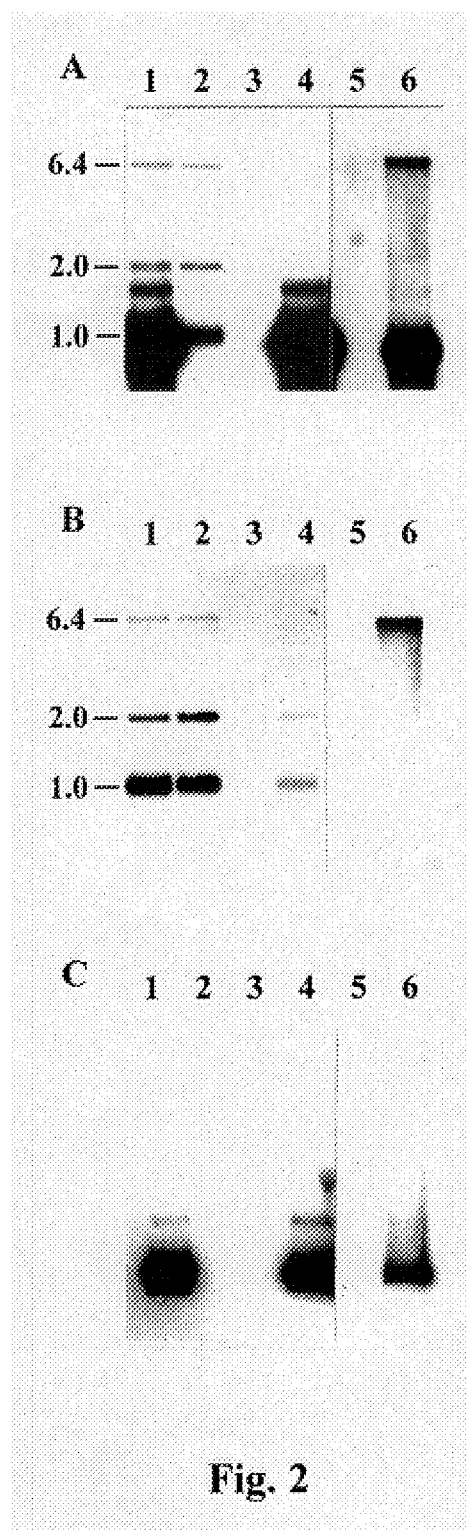
FIG. 2. Northern blot analysis of the replication dependency of sBaMV RNA in barley protoplasts. Barley protoplasts were inoculated with (1) BaMV-V RNA, (2) BaMV-L RNA, (3) sBaMV RNA, (4) mixture of BaMV-L and sBaMV RNA or (5) distilled water. Lane 6 is viral RNAs extracted from purified BaMV-V virions for size markers. After incubation of inoculated protoplasts for 24 hr, total nucleic acids were extracted, electrophoresed, and transferred to H-Bond hybridization membrane. The membrane was individually hybridized with (A) the mixture of L- and S- cDNA probes, (B) L-cDNA probe or with (C) S-cDNA probe as described in the legend of FIG. 1. The RNA sizes are shown in kb and the position of sBaMV RNA is indicated by an arrow.

Protoplasts were inoculated with single RNAs or a combination of L and s BaMV RNAs, harvested 24 hr.

postinfection, and assayed for the RNA accumulation by Northern blot analysis. In each experiment, three parallel blots were separately hybridized with L-, S- and mixed cDNA probes. As shown in FIG. 2, in barley protoplasts inoculated with unfractionated BaMV-V RNA, a mixture of L- and S-cDNA probes detected high level of L and sBaMV RNA replication (FIG. 2A, lane 1). The genomic and two major subgenomic RNAs, 2.0 and 1.0 kb, were observed when the L-cDNA probe was used alone (FIG. 2B, lane 1). The S-cDNA probe detected a sBaMV RNA monomer at a very high concentration and possibly a slowly migrating dimer at a low concentration (FIG. 2C, lane 1). When the protoplasts were inoculated with RNA from the BaMV-L isolate, only genomic RNA and two subgenomic RNAs were detected (FIGS. 2A and 2B, lane 2). No detectable sBaMV RNA was observed when the S-cDNA probe was used alone (FIG. 2C, lane 2). The absence of sBaMV replication was also observed in protoplasts inoculated with sBaMV only, no matter which kind of probe(s) was used (FIG. 2A, 2B and 2C, lane 3), indicating that sBaMV cannot replicate by itself. However, the presence of L, two subgenomic and sBaMV were detected in the protoplasts inoculated with the mixture of L and sBaMV RNAs (FIG. 2A, 2B and 2C, lane 4). No RNAs were ever detected in the mock-inoculated protoplasts (FIG. 2A, 2B and C, lane 5). RNAs from purified BaMV-V virions are shown as markers (FIG. 2A, 2B and c, lane 6).

EXAMPLE 3 cDNA Synthesis of sBaMV, Cloning and Sequencing

The first strand cDNA was synthesized by avian myeloblastosis virus reverse transcriptase using gel-eluted sBaMV as a template and oligonucleotide $(dT)_{15}$-XbaI as a primer. The reaction condition for synthesis of the first and second strand cDNA followed the instructions of the Riboclone cDNA synthesis kit (Promega). After the double strand cDNA was synthesized, it was cut with XbaI, ligated into the SmaI and XbaI site of the pUC119, and then transformed into E. coli. DH5∝. Colonies containing plasmids with sBaMV-specific inserts were selected by Southern hybridization using S-cDNA as a probe (Molecular Cloning. 2nd Ed. Cold Spring Harbor Laboratory Press).

A plasmid (designated as pBSNL2) selected by S-cDNA probe contains a cDNA insert of 839 bp including 17 poly (A) residues at the 3' end but lacks the sequence corresponding to the 5' end 14 nts of sBaMV. Dideoxynucleotide chain termination method (Proc. Natl. Acad. Sci. USA 74: 5463–5467, 1977) was used to determine the 839 bp sequence of the insert on both cDNA strands. The sequence at the 5' end of sBaMV was directly determined by RNA sequencing, using gel-eluted sBaMV RNA as a template, oligonucleotide primer complementary to the residues 36 to 50 (3' TCTTTGTGATCGGT 5') to prime reverse transcription reaction in the presence of dideoxyribonucleotide and terminal deoxynucleotidyl transferase (Anal. Biochem. 157: 275–282, 1986; Nucl. Acid. Res. 18: 6162, 1990).

As shown in FIG. 3, the complete nucleotide sequence of sBaMV RNA is 836 nts, excluding the poly (A) tail. It has a base composition of 25.5% A, 29.3% C, 24.8% G and 20.4% U. A large ORF is present in the genome of sBaMV. It commences at the first AUG following a 159 nt non-coding sequence and ends at nucleotide 709 with a UGA termination codon. This ORF encodes a 183- amino acid polypeptide of M, 20,154. The complete nucleotide sequence of sBaMV is terminated by a non-coding region of 125 nts and a poly (A) tail. A polyadenylation signal AAUAAA is found in the 3' region of sBaMV. The first six nts, GAAAAC, is in common with that of BaMV genomic RNA (J. Gen. Virol. 75: 2513–2518, 1994). Other limited sequence similarities between these two genomes are scattered in the 5' terminal region. Compared to the sequences deposited to the EMBL/GenBank Data Libraries, this novel satellite RNA shares no sequence homology with any known genes, viruses, or satellite RNAs. The Accession No. for sBaMV L22762 was given.

EXAMPLE 4

In Vitro Translation and Immunoprecipitation

The in vitro translation of RNA samples was performed in rabbit reticulocyte lysate (Promega) as described previously (Phytopatholoty 82: 731–734, 1992). The translated products and immunoprecipitates with anti-BaMV capsid protein were analyzed on a 8–20% linear gradient SDS-polyacrylamide gel, and detected by fluorography (Eur. J. Biochem. 46: 83–88, 1974).

Figure 4:
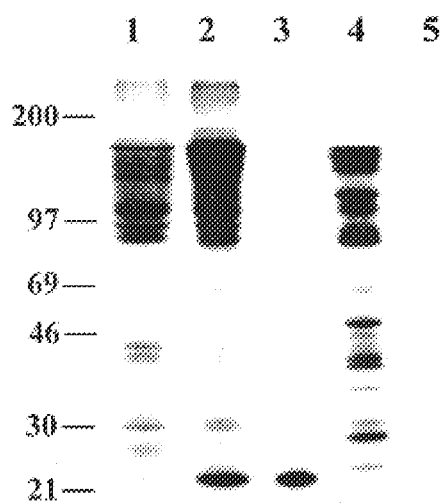
FIG. 4. Electrophoretic analyses in a 8–20% SDS-polyacrylamide gel of the translation products of viral RNAs in the rabbit reticulocyte lysate. BaMV-O RNA (lane 1), BaMV-V RNA (lane 2), gel-eluted sBaMV RNA (lane 3), BaMV-L RNA (lane 4) or no RNA (lane 5) was added to the lysate. Lane 1 shows size markers as indicated on the left.

As shown in FIG. 4, both BaMV-O and BaMV-V RNAs directed the synthesis of a major polypeptide with M, 160 kDa (lane 1 and 2). However, a major additional polypeptide of about 25 kDa was synthesized in the BaMV-V RNA directed translation system (lane 2). Gel-eluted sBaMV RNA also efficiently directed the synthesis of a polypeptide with the same electrophoretic mobility (lane 3). The pattern of translation products of BaMV-L RNA (lane 4), was similar to that of BaMV-V RNA (lane 2) except that it showed no 25 kDa protein. These results indicate that sBaMV RNA codes for a protein migrating electrophoretically at a molecular weight of 25 kDa. This is different from the 20 kDa protein predicted from nucleotide sequence analysis. This discrepancy may be due to its highly basic character (PI=10.25) resulting in the change of mobility in the gel electrophoresis.

In the immunoprecipitation reaction, all of the translated products from the BaMV-V RNA and the BaMV-O RNA did not react with the anti-BaMV capsid protein serum indicating that the protein synthesized from sBaMV is immunologically unrelated to the BaMV capsid protein.

All the results as shown above, including Northern hybridization, inoculation, nucleotide sequencing, and in vitro translation reaction, confirm that sBaMV is neither the subgenomic RNA of BaMV nor the defective interfering RNA molecules, but a satellite RNA associated with BaMV which can replicate only in the presence of BaMV genomic RNA. Furthermore, this satellite RNA has the capacity of encoding a 20 kDa protein, which is quite different from the small satellite RNAs that have no obvious ORFs.

EXAMPLE 5

Construction of Full-Length Infectious cDNA Clone of sBaMV

Using gel-purified sBaMV RNA as template and oligonucleotides (5'GTCGACTCTAGA (T) 15) as a primer, the first strand of the cDNA was synthesized according to the method described above. The second-strand cDNA was synthesized by T4 DNA polymerase and primer (5'GCCTGCAGTAATACGACTCACTATAGAAAACTC-ACCGCAACGA) (including T7 RNA polymerase promoter) (Mol. Cell Biol. 4:2876–2882, 1984). Full length cDNA was isolated from low-melting point agarose gels, cut with PstI and XbaI, ligated to the PstI and XbaI sites of pUC119, and then transformed into E. Coli DH5a. After screening, clone pBSF4 was identified to contain the full-length cDNA of sBaMV and 17 3'terminal(A) residues (designated as pBSF4).

The in vitro transcripts of pBSF4 (designated as BSF4) were synthesized in an in vitro transcription reaction by XbaI-linearized pBSF4 (*J. Virol.* 61: 1457–1465, 1987).

Figure 5:
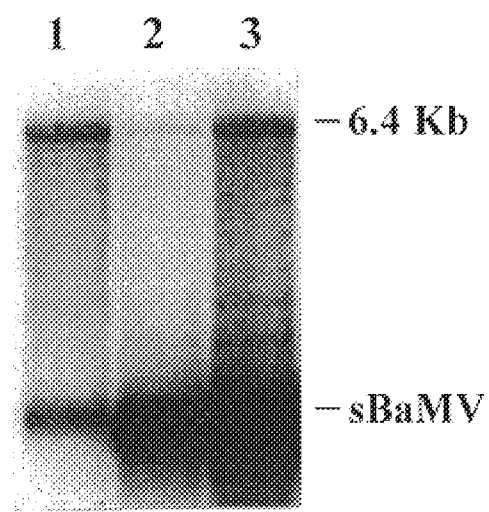
FIG. 5. Northern blot replication analyses of sBaMV synthetic transcript in *C. quinoa* leaves co-inoculated with BaMV-L RNA. Leaves were inoculated with BaMV-L RNA alone (lane 1), together with native sBaMV (lane 2), or with transcript bSF4 (lane 3). Seven days after inoculation, purified virion RNA from 0.05 g of infected leaves were glyoxylated, electrophoresed through 1% agarose, and transferred to a nylon membrane. Blots were hybridized with a mixture of $^{32}$p-labeled L and S cDNA probe.

The infectivity of synthetic capped transcripts BSF4 was tested in *C. quinoa*. For each inoculation, the mixture contains the transcripts synthesized from 0.6 μg of the linearized DNA template and 1 μg of BaMV-L RNA diluted in 200 μl of sterilized distilled water. A mixture of 1 μg of native sBaMV and BaMV-L RNA was consistently used as a positive control. Approximately ten days after inoculation, the inoculated leaves were harvested for virion purification and RNA extraction (*Phytopatholoy* 81: 1551–1555, 1991). The levels of progeny RNA in the inoculated leaves were analyzed by Northern hybridization (*Phytopathology* 82: 731–734, 1992). As shown in FIG. 5, Northern blot analysis with the mixture of L and S probes detected the 6.4 kb genomic RNA and sBaMV-specific sequences in virion preparations from *C. quinoa* leaves co-inoculated with BaMV-L RNA and BSF4 (lane 3). The level of RNA accumulation was similar to or higher than those coinoculated with native sBaMV (lane 2). Viral RNA and 1.0 kb encapsidated subgenomic RNA were detected in BaMV-L RNA inoculated leaves alone (lane 1). The results suggested that synthetic transcripts of sBaMV are biologically active in plants coinoculated with the genomic RNA.

EXAMPLE 6

Constructions of sBaMV Mutants and Their Activity Assay

Figure 6:
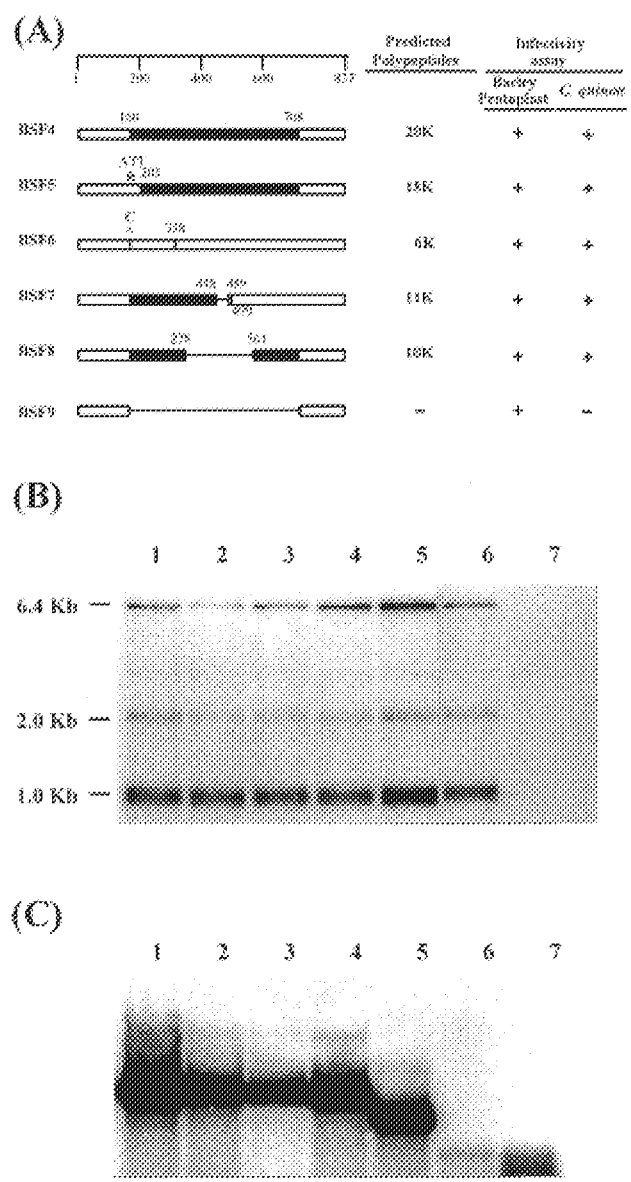
FIG. 6. Summary of the construction and activity of sBaMV mutants: (A) A schematic diagram of sBaMV mutants and their altered coding capacity and ability to replicate in barley protoplasts and *C. quinoa* plants; (B,C) Accumulation of BaMV genomic RNA and sBaMV RNA derivatives in infected protoplasts. Northern blot analyses of total RNAs isolated from 3×10$^4$ barley protoplasts 24 hr post-infection with BaMV-L RNA and sBaMV mutants indicated above each lane. F9 only, BSF9 transcript inoculated only. (B) Genomic and subgenomic RNAs were detected by $^{32}$p-labeled L cDNA probe. Positions of baMV genomic and subgenomic RNAs are indicated to the left. (C) sBaMV RNA was detected by the $^{32}$p-labeled S cDNA probe.

Oligonucleotide-directed mutagenesis in the N-terminal region of the 20 kDa protein gene was performed using the pBSF4 as a template (*Methods Enzymol.* 154: 367–382, 1987). The changes in the mutagenized clones were verified by restriction fragment analysis and complete nucleotide sequencing to avoid possible mutations that might have been introduced elsewhere in the cloned cDNA (FIG. 6A).

(1) pBSF5: The first initiation codon 160AUG; and the second in-frame initiation codon was downstream at nucleotide 205 of sBaMV that encodes a 18 kDa protein;

(2) pBSF6: A frameshift mutant in which a cytosine was inserted after the first initiation codon 160^AUG resulting in the premature termination of a 6 kDa protein downstream;

(3) pBSF7: 40 nucleotide were deleted from nucleotide 449 to nucleotide 488 that led to a premature termination of a 11 kDa protein;

(4) pBSF8: 282 nucleotide were deleted from nucleotide 279 to nucleotide 560 that led to a deletion of 94 amino acids; and (5) pBSF9: A large deletion mutant in which the satellite ORF was completely removed.

Transcripts of the mutants were transcribed as previously described and their activities were assayed in the barley protoplasts inoculated with the presence of BaMV-L genomic RNA. As shown in FIG. 6B and 6C, Northern blot analysis of total RNAs extracted from protoplasts revealed that all of the mutants were able to replicate in cells in the presence of BaMV RNA, as evidenced by the production of slower migration dimer bands (FIG. 6C). Mutations at either the N-termini or internal ORF of satellite protein gene caused a slight decrease in activity ranging from 21 to 55% as compared with the wild-type BSF4. However, deletion of the entire ORF of sBaMV in BSF9 substantially reduced the replication activity to the very low level of about 0.5–1% of BSF4. The low accumulation of the transcripts may have been due to the complete removal of ORF resulting in the change of RNA conformation and stability (*J. Virol.* 68: 8466–8469, 1994). Moreover, analyses of progeny RNA of the mutants by PCR cDNA amplication and nucleotide sequencing revealed that all mutants still remained the mutated sizes or sequences in the progeny (data not shown). This excluded the possibility of contamination of wild-type transcripts BSF4 or native sBaMV in the infection. Thus, all the results suggested an inessential role of the satellite-encoded protein in the replication of sBaMV.

EXAMPLE 7

Construction of Chimeric Hybrid of sBaMV

Figure 7:
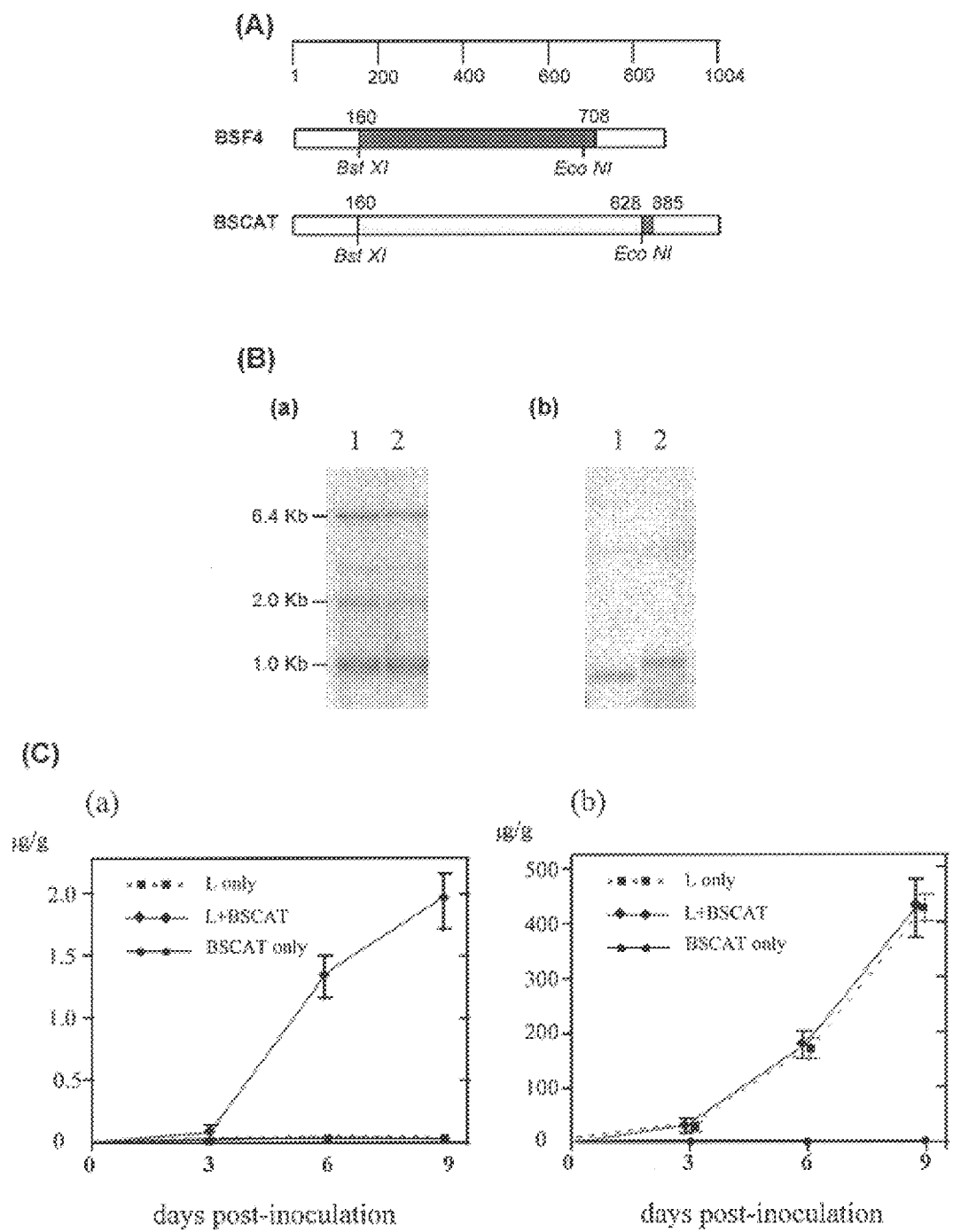
FIG. 7. Schematic diagram, Northern analysis and the CAT expression of chimeric BSCAT in *C. quinoa* leaves inoculated with BaMV-L RNA: (A) Structure of wt pBSF4 and pBSCAT mutant; (B) Northern blot analysis of purified virion RNA from 0.05g of *C. quinoa* leaves 7 days after infection with BaMV-L RNA plus BSF4 or BSCAT as indicated. The RNA accumulation of (a) genomic and subgenomic RNAs or (b) satellite RNA was assessed with the same probes as in FIG. 1. Autoradiographs were printed by PhosphorImager (Molecular Dynamics, Sunnyvale, Calif.). (C) the ELISA assay CAT (a) and BaMV capsid protein (b) of total protein extracts from infected *C. quinoa* leaves inoculated with BaMV-L RNA alone, BSCAT transcripts alone, or a mixture of BaMV-L RNA and BSCAT transcripts.
Figure 8:
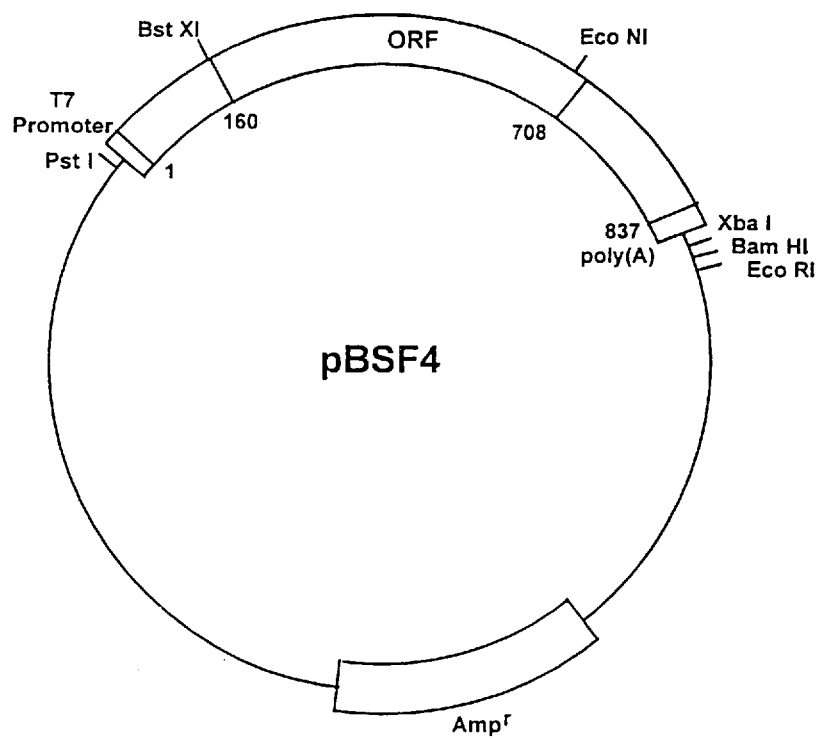
FIG. 8. The schematic diagram of the restriction map of the plasmid pBSF4.

Since the sBaMV-encoded protein is not required for its replication, the chimeric plasmid pBSCAT was constructed by substituting the CAT coding sequences for the ORF of pBSF4 (FIG. 7A). To generate the chimeric mutant pBSCAT, the DNA fragment corresponding to the CAT ORF was amplified with two primers: BSCAT1 (5'-TATCCAAGACGATGGAGAAAAAATC-3') and BSCAT2 (5'-CAGCCTCTGGGAGGTTACGCCCCGCCCTG-3') from pCM7 (Progema Corp., Madison, Wis.) by 30 cycles of polymerase chain reaction (PCR) (*Science* 230: 1350–1354, 1988). A single cycle consisted of 45 sec. at 94° C. for denaturation, 45 sec. at 55° C. for annealing, and 1 min. at 72° C. for elongation. pBSCAT was constructed by replacing the BstXI and EconNI ORF cassettes of pBSF4 with the amplified CAT ORF, and was also digested with BstXI and EcoNI (FIG. 7A).

The in vitro hybrid transcripts of BSCAT, along with BaMV-L genomic RNA, were coinoculated *C. quinoa* leaves. Seven days after inoculation, the viruses were purified and the RNAs were extracted. As shown in FIG. 7B, the accumulated level of BSCAT is closed to that of BSF, indicating that chimeric transcripts replicated efficiently in the plants and were encapsidated by the viral capsid proteins.

In order to measure the CAT expression of BSCAT in plants, BaMV-L *C. quinoa* leaves were co-inoculated with BaMV-L RNA and BSCAT transcripts. Approximately ten days after inoculation, inoculated *C. quinoa* leaves were harvested, ground in 4× (V/W) volume of 0.5M borate buffer, pH 9.0, with 1 mM EDTA and 0.5% 2-mercaptoethanol, and then filtrated with 2 layers of miracloth. The filtrate was added with Triton X-100 to have a final concentration of 2%, stirred for 10 min. and subjected to low-speed centrifugation. To the supernatant, 2× volume of methanol containing 0.1M $NH_4Cl$ was added, mixed thoroughly, and incubated at–70° C. for 2 hr or at –20° C. overnight. After centrifugation, the portions of supernatant were immunoassayed for CAT enzyme following the manufacture's instructions (CAT ELISA, Boehringer Mannheim GmbH, Mannheim, Germany).

As shown in FIG. 7C, considerable CAT activity was detected in extracts of *C. quinoa* leaves coinoculated with BaMV-L RNA and BSCAT transcript by CAT-ELISA assay. Using standard CAT enzyme for calibration, 2.0 μg of CAT enzyme were produced per gram of *C. quinoa* leaves. Control samples coinfected with BSCAT transcripts or BaMV-L RNA alone exhibited CAT activity only in the background level (FIG. 7C).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 837 base pairs
        ( B ) TYPE: nucleic acid
        ( C ) STRANDEDNESS: single
        ( D ) TOPOLOGY: linear ( i i ) MOLECULE TYPE: RNA (Satellite)

( i i i ) HYPOTHETICAL: N ( i v ) ANTI-SENSE: N ( v ) ORIGINAL SOURCE:
        ( A ) ORGANISM: Bambusa vulgaris McClure
        ( B ) INDIVIDUAL ISOLATE:
        ( G ) CELL TYPE:

( x i ) SEQUENCE DESCRIPTION: SEQ ID NO:1:

```
gaaaactcac  cgcaacgaaA  CGAAACAAAT  CGTTCAGAAA  CACTAGACCA  CGAGGGCCCC    60
CCTATAGTCC  CGCTGAGGGT  GTGGCAGGCC  CCGTGCGATA  GGCTAACTGT  GGTGTTCCCC   120
GCACTCCGTC  GAGCGGTTAA  TACGACGCTT  ACCAAGACGA  TGGTTCGGAG  GAGAAATCGT   180
CGCCAGAGAT  CGCGTGTCTC  CCAAATGACC  GACATCATGT  ATGGCTCACT  AACACTGGGC   240
AGTACCACAA  CATGGACCAG  GAAGAATTTC  CCTGGGTTGG  CCAATATGGG  AGATCGACCT   300
TTCCAGGTCA  TCTCTGTTAA  AATTGTTGTC  TCGTCTGCCT  CCCCCATGCT  TTACCAAGCC   360
AGGCTTTACT  CACCACACGA  TGATGACAAT  GTGGGGTCCA  CCGGGCTTCA  AATGTCTGGA   420
ACCACTCCAC  ACACTCACCA  TATGAGAGCT  CTGCCAGGTC  AAAACACCTG  GTTTAGTGGC   480
AACACGAGCT  CTACTCAGGT  GATTGTCGCC  ATTGATGGCC  TGAAGACGAA  GACAACGGAT   540
GCCACGCCCC  AGAACGCGGT  GGCCGTTCAG  GTGTTCTATC  GAGTGGCGCC  GAGCGAACTC   600
CAGAGCGCAA  CTGGTAATGC  TGAAATGCCT  ACAACCACGC  CTTTTGACCT  CCCAGAGGGG   660
TATGAATACC  TCGCTGACGC  GTGGCTCCCT  GACCGTGCAC  CAACCAGTTG  ATCCACGAGC   720
ACAACCGGCT  TGTCAATGAG  CCGCCAGGTT  TAGCCTGGTT  CCACATTGAC  CCACCACCCA   780
TACTATGAGA  CCTAACCAGT   AGTGGTGGTC  GTCCCGAATA  AAGACGCTAA  AAGATGA     837
```

( 2 ) INFORMATION FOR SEQ ID NO:2:

( i ) SEQUENCE CHARACTERISTICS:
        ( A ) LENGTH: 183 amino acids
        ( B ) TYPE: amino acid
        ( D ) TOPOLOGY: linear ( i i ) MOLECULE TYPE: protein ( i x ) FEATURE:
        ( A ) NAME/KEY:
        ( B ) LOCATION:
        ( D ) OTHER INFORMATION:

( x i ) SEQUENCE DESCRIPTION: SEQ ID NO:2:

```
Met  Val  Arg  Arg  Arg  Asn  Arg  Arg  Gln  Arg  Ser  Arg  Val  Ser  Gln  Met
                     5                    10                       15
Thr  Asp  Ile  Met  Tyr  Gly  Ser  Leu  Thr  Leu  Gly  Ser  Thr  Thr  Thr  Trp
                    20                    25                       30
```

-continued

| | | | | | | | | | | | | | | |
|---|---|---|---|---|---|---|---|---|---|---|---|---|---|---|
| Thr | Arg | Lys<br>35 | Asn | Phe | Pro | Gly | Leu<br>40 | Ala | Asn | Met | Gly | Asp<br>45 | Arg | Pro | Phe |
| Gln | Val<br>50 | Ile | Ser | Val | Lys | Ile<br>55 | Val | Val | Ser | Ser | Ala<br>60 | Ser | Pro | Met | Leu |
| Tyr<br>65 | Gln | Ala | Arg | Leu | Tyr<br>70 | Ser | Pro | His | Asp | Asp<br>75 | Asn | Val | Gly | Ser<br>80 |
| Thr | Gly | Leu | Gln | Met<br>85 | Ser | Gly | Thr | Thr | Pro<br>90 | His | Thr | His | His | Met<br>95 | Arg |
| Ala | Leu | Pro | Gly<br>100 | Gln | Asn | Thr | Trp | Phe<br>105 | Ser | Gly | Asn | Thr | Ser<br>110 | Ser | Thr |
| Gln | Val | Ile<br>115 | Val | Ala | Ile | Asp | Gly<br>120 | Leu | Lys | Thr | Lys | Thr<br>125 | Thr | Asp | Ala |
| Thr | Pro<br>130 | Gln | Asn | Ala | Val | Ala<br>135 | Val | Gln | Val | Phe | Tyr<br>140 | Arg | Val | Ala | Pro |
| Ser<br>145 | Glu | Leu | Gln | Ser | Ala<br>150 | Thr | Gly | Asn | Ala | Glu<br>155 | Met | Pro | Thr | Thr | Thr<br>160 |
| Pro<br>165 | Phe | Asp | Leu | Pro | Glu<br>170 | Gly | Tyr | Glu | Tyr | Leu<br>175 | Ala | Asp | Ala | Trp | Leu<br>180 |
| Pro | Asp | Arg | Ala | Pro<br>185 | Thr | Ser | | | | | | | | | |

We claim:

1. A purified and isolated viral satellite RNA for use as a vector for plant foreign gene expression which consists of the sequence shown in FIG. 3 (SEQ ID:1).

2. The satellite RNA of claim 1 wherein said RNA is prepared from a potexvirus.

3. The satellite RNA of claim 1 wherein said RNA is an isolate from a bamboo mosaic virus (BaMV).

4. The satellite RNA of claim 1 wherein said RNA has the EMBL/GenBank Accession No. L22762.

5. The satellite RNA of claim 1 wherein said RNA contains an open reading frame (ORF) commencing at nucleotide 160 of SEQ ID:1 and ending at nucleotide 709 of SEQ ID:1 with a UGA termination codon.

6. The satellite RNA of claim 5 wherein said ORF encodes a polypeptide having a sequence as shown in FIG. 3 (SEQ ID:2).

7. The satellite RNA of claim 6 wherein said polypeptide has a predicted molecular weight of 20,154.

8. The satellite RNA of claim 1 wherein translation of said RNA in an in vitro translation assay results in the synthesis of a polypeptide having a molecular weight of 25 kDa as determined on an SDS-polyacrylamide gel.

9. The satellite RNA of claim 8 wherein said polypeptide has a calculated PI value of 10.25.

10. A method of infecting a plant with a viral satellite RNA which comprises mechanically inoculating a sufficient quantity of a mixture containing a viral satellite RNA according to claim 1 and a potexvirus viral genomic RNA onto the plant.

11. The method of claim 10 wherein said viral satellite and genomic RNAs are prepared from BaMV.

12. A DNA molecule of single or double strands having one strand with a sequence complementary to the viral satellite RNA sequence of claim 1.

13. A plasmid which produces infectious viral satellite RNA virions for plant infection in the presence of a BaMV genomic RNA, said plasmid comprising a cDNA clone comprising a DNA molecule identical to the DNA molecule of claim 12.

14. The plasmid of claim 13 wherein said plasmid is pBSF4.

15. The plasmid of claim 14 wherein said plasmid produces a full length infectious mRNA of a satellite RNA from Bamboo Mosaic Virus (sBaMV).

16. The plasmid of claim 15 wherein said plasmid produces infectious symptoms in plants approximately 10 days after inoculation.

17. The plasmid of claim 13 wherein said plasmid infects either a monocot or a dicot plant.

18. A method of constructing a plasmid comprising an infectious cDNA clone which produces infectious viral satellite RNA virions for plant infection in the presence of a BaMV genomic RNA, comprising:
   a) synthesizing a first strand cDNA using the sBaMV RNA sequence of FIG. 3 (SEQ ID:1) as a template;
   b) synthesizing a second strand DNA complementary to a);
   c) isolating and ligating the DNA from b) into a plasmid vector;
   d) transforming a host with the plasmid from c); and
   e) selecting a clone which produces infectious DNA.

19. The method of claim 18 wherein said plasmid vector of step c) is pUC119.

20. The method of claim 18 wherein said host is *E. coli* DH5-alpha.

21. The method of claim 18 wherein said plasmid is pBSF4.

22. A method of infecting a plant with cDNA clones which produce a viral satellite RNA comprising:
   a) conducting an in vitro transcription of the clone of claim 18;
   b) inoculating a sufficient quantity of a mixture containing the transcripts of a) with a potexvirus viral genomic RNA onto the plant.

23. A plasmid comprising a DNA molecule whose transcript self-replicates in a plant host when said transcript is co-inoculated with a genomic RNA prepared from a potexvirus, said DNA selected from the group consisting of:

a) the DNA molecule as set out in claim 12, and its complementary strand; and b) a DNA molecule which comprises a sequence which encodes the amino acid sequence of SEQ ID:2.

24. The plasmid of claim 23 wherein said plasmid is further subject to mutagenesis to produce mutant DNA molecules whose transcripts self-replicate in a plant host when co-inoculated with a genomic RNA prepared from a potexvirus, said mutant DNA selected from the group consisting of:

a) the DNA molecule defined in claim 23 except that the nucleotide sequence encoding the first initiation codon (corresponding to 160-AUG of SEQ ID:1) is changed to AUU b) the DNA molecule defined in claim 23 except that a frameshift mutation is effected to said DNA molecule by inserting a cytosine one base after the first initiation codon (corresponding to 160-AUG of SEQ ID:1);

c) the DNA molecule defined in claim 23 except that nucleotides corresponding to nucleotides 449 to 488 of SEQ ID:1 are deleted from said DNA molecule;

d) the DNA molecule defined in claim 23 except that nucleotides corresponding to nucleotides 279 to 560 of SEQ ID:1 are deleted from said DNA molecule;

e) the DNA molecule defined in claim 23 except that the nucleotides encoding SEQ ID:2 are deleted; and f) the DNA molecule defined in claim 23 except that said DNA molecule is mutagenized such that any deletions, interruptions, or alterations do not result in a DNA molecule which is shorter than the DNA defined in e).

25. The plasmid of claim 24 wherein said plasmid is selected from the group consisting of pBSF5, pBSF6, pBSF7, pBSF8 and pBSF9.

26. A viral vector which expresses a foreign gene in plants when co-inoculated with a genomic RNA prepared from a potexvirus, comprising:

a) a first DNA molecule which is complementary to the RNA molecule set forth in claim 1 except that the DNA sequence between nucleotides 160 and 790 of SEQ ID:1 is partially or completely removed and replaced with a foreign gene of desire; and b) at least one regulatory DNA sequence to which the first DNA molecule is operably linked.

27. The viral vector of claim 26 wherein the potexvirus is a bamboo mosaic virus (BaMv).

28. The viral vector of claim 26 wherein the vector is a satellite RNA from the bamboo mosaic virus (sBaMV RNA).

29. The viral vector of claim 26 wherein the regulatory sequence is a T7 RNA polymerase promoter.

30. The viral vector of claim 26 wherein the foreign gene contains a DNA sequence encoding chloramphenicol acetyl transferase (CAT).

31. The viral vector of claim 30 wherein said vector is pBSCAT.

32. A method of achieving foreign gene expression in plants using a satellite RNA from potexvirus as a vector, comprising:

a) preparing the viral vector of claim 26 according to the method of claim 18; and b) inoculating a plant according to the method of claim 22.

33. The method of claim 32 wherein the potexvirus is an isolate of BaMV.

34. The method of claim 32 wherein the plants are either monocots or a dicots.

35. A method of achieving foreign gene expression to produce a pharmacological or pharmaceutical activity in plants using a satellite RNA from potexvirus as a vector, comprising:

a) preparing the viral vector of claim 26 according to the method of claim 18; and b) inoculating a plant according to the method of claim 22.

36. The method of claim 35 wherein the foreign gene is expressed within 10–14 days after inoculation.

* * * * *